(12) United States Patent
Hoffman et al.

(10) Patent No.: US 8,633,691 B2
(45) Date of Patent: Jan. 21, 2014

(54) LIQUID COMPOSITIONS AND USES THEREOF FOR GENERATING DIFFUSION ORDERED NMR SPECTRA OF MIXTURES

(75) Inventors: Roy Hoffman, Maale Adumim (IL); Nissim Garti, Jerusalem (IL); Abraham Aserin, Jerusalem (IL); Chava Pemberton, Jerusalem (IL)

(73) Assignee: Yissum Research Developemtn Comapny of the Hebrew University of Jerusalem, Jerusalem (IL)

( * ) Notice: Subject to any disclaimer, the term of this patent is extended or adjusted under 35 U.S.C. 154(b) by 425 days.

(21) Appl. No.: 13/060,543

(22) PCT Filed: Sep. 1, 2009

(86) PCT No.: PCT/IL2009/000841
§ 371 (c)(1),
(2), (4) Date: May 20, 2011

(87) PCT Pub. No.: WO2010/023673
PCT Pub. Date: Mar. 4, 2010

(65) Prior Publication Data
US 2011/0215806 A1 Sep. 8, 2011

Related U.S. Application Data

(60) Provisional application No. 61/093,403, filed on Sep. 1, 2008.

(51) Int. Cl.
*G01V 3/00* (2006.01)
(52) U.S. Cl.
USPC .......................................... 324/307; 324/309

(58) Field of Classification Search
USPC ........ 324/300–322; 600/407–445; 436/6, 524
See application file for complete search history.

(56) References Cited

U.S. PATENT DOCUMENTS

2007/0104648 A1* 5/2007 Shull .............................. 424/9.3

FOREIGN PATENT DOCUMENTS

| FR | 2 847 674 A1 | 5/2004 |
| JP | 2001-328992 A | 11/2001 |
| WO | 2005/001206 A1 | 1/2005 |
| WO | 2008/050347 A2 | 5/2008 |
| WO | 2009/036741 A1 | 3/2009 |

OTHER PUBLICATIONS

Morris, et al., "Resolution of Discrete and Continuous Molecular Size Distributions by Means of Diffusion-Ordered 2D NMR Spectroscopy," J. Am. Chem. Soc., (1993), pp. 4291-4299, vol. 115.
Schilling, et al., "NMR-Chromatographie—DOSY," GIT Labor-Fachzeitschrift, (2002), p. 1163, vol. 46.

(Continued)

*Primary Examiner* — Brij Shrivastav
(74) *Attorney, Agent, or Firm* — Vorys, Sater, Seymour and Pease LLP; Susanne M. Hopkins (57) ABSTRACT

Provided are homogeneous liquid systems substantially $^1$H-NMR inactive and/or devoid of protons and are capable of enhancing the diffusion separation of a mixture, the system is substantially devoid of at least one NMR active nucleus present in the mixture. Further provided are methods of using the homogeneous liquid systems for enhancing the diffusion separation of a mixture and/or generating a diffusion ordered spectrum of a mixture and/or minimizing the peak width in a liquid state diffusion ordered spectrum of a mixture.

19 Claims, 5 Drawing Sheets

(56) References Cited

OTHER PUBLICATIONS

Pages, et al., "Investigation of the Chromatographic Process via Pulsed-Gradient Spin-Echo Nuclear Magnetic Resonance. Role of the Solvent Composition in Partitioning Chromatography," Anal. Chem. (2006), pp. 561-566, vol. 78.

Hoffman, et al., "High-Resolution NMR "chromatography" using a liquids spectrometer," J. Magn. Reson., (2008), pp. 295-299, vol. 194.

Callaghan, et al., "Diffusion-diffusion correlation and exchange as a signature for local order and dynamics," J. Chem. Phys., (2004), pp. 4032-4038, vol. 120, No. 8.

Qiao, et al., "Diffusion Correlation NMR Spectroscopic Study of Anisotropic Diffusion of Water in Plant Tissues," Biophys. J., (2005), pp. 2899-2905, vol. 89.

Song, et al., "T1-T2 Correlation Spectra Obtained Using a Fast Two-Dimensional Laplace Inversion," (2002), pp. 261-268, vol. 154.

Qiao, et al., "Diffusion exchange NMR spectroscopic study of dextran exchange through polyelectrolyte multilayer capsules," J. Chem. Phys., (2005), pp. 214912-1-214912-9, vol. 122.

Nilsson, et al., "Improving Pulse Sequences for 3D Diffusion-Ordered NMR Spectroscopy: 2DJ-IDOSY," Anal. Chem., (2004), pp. 5418-5422, vol. 76.

Jerschow, et al., "3D Diffusion-Ordered TOCSY for Slowly Diffusing Molecules," J. Magn. Reson. A, (1996), pp. 222-225, vol. 123.

Gozansky, et al., "DOSY-NOESY: Diffusion-Ordered NOESY," J. Magn. Reson. B, (1996), pp. 94-96, vol. 111.

Barjat, et al., "A Three-Dimensional DOSY-HMQC Experiment for the High-Resolution Analysis of Complex Mixtures," J. Magn. Reson., (1998), pp. 131-138, vol. 131.

Buevich, et al., "Residue-Specific Real-Time NMR Diffusion Experiments Define the Association States of Proteins during Folding," Am. Chem. Soc., (2002), pp. 7156-7162, vol. 124.

Birlirakis, et al., "A New Approach in the Use of Gradients for Size-Resolved 2D-NMR Experiments," J. Am. Chem. Soc., (1996), pp. 13083-13084, vol. 118.

Wu, et al., "Heteronuclear-Detected Diffusion-Ordered NMR Spectroscopy through Coherence Transfer," J. Magn. Reson. A, (1996), pp. 215-218, vol. 123.

Odinstov, et al., "Molecular Diffusion and DNP Enhancement in Aqueous Char Suspensions," J. Magn. Reson., (1998), pp. 435-443, vol. 135.

Kogan, et al., "Microemulsion-Facilitated Crystallization of Carbamazepine," J. Disp. Sci. Tech., (2007), pp. 1008-1019, vol. 28.

Zielinski, et al., "Using perdeuterated surfactant micelles to resolve mixture components in diffusion-ordered NMR spectroscopy," Magnetic Resonance in Chemistry, (2009), p. 56, vol. 47, No. 1.

Bilia, et al., "A Diffusion-Ordered NMR Spectroscopy Study of the Solubilization of Artemisinin by Octanoyl-6-O-ascorbic Acid Micelles," Journal of Pharmaceutical Sciences, (2002), pp. 2265-2270, vol. 91, No. 10.

* cited by examiner

LIQUID COMPOSITIONS AND USES THEREOF FOR GENERATING DIFFUSION ORDERED NMR SPECTRA OF MIXTURES

This is a National Phase Application filed under 35 U.S.C. 371 as a national stage of PCT/IL2009/000841, filed on Sep. 1, 2009, an application claiming the benefit under 35 USC 119(e) of U.S. Provisional Application No. 61/093,403, filed on Sep. 1, 2008, the content of each of which is hereby incorporated by reference in its entirety.

FIELD OF THE INVENTION

This invention relates to liquid systems and uses thereof in diffusion ordered NMR spectroscopy.

BACKGROUND OF THE INVENTION

When carrying out a chemical reaction, be it an industrial process or a research experiment, one starts with a number of reactants and, in some cases, obtains a mixture of various products with or without traces of the starting reactants. Usually, this requires tedious separation of each constituent of the mixture yielded and only then identification of each product obtained.

NMR spectroscopy is an excellent method for examining the molecular structure of pure compounds. However, it is limited when examining mixtures of compounds. To a certain extent 2D and multidimensional NMR can separate simple mixtures but a more suitable method is to separate the components according to their diffusion coefficients.

The diffusion ordered spectroscopy (DOSY) method (Morris et al, J. Am. Chem. Soc., 115, 4291-4299 (1993)) can separate compounds in a mixture and with the correct processing can ideally yield regular 1D-spectra for each compound in the mixture (Schilling et al. *GIT Labor-Fachzeitschrift*, 46, 1163. (2002)). One of the problems associated with this method is that in most cases there is insufficient separation in the diffusion axis to fully separate the compounds in the mixture.

An attempt to enhance the separation in the diffusion dimension was made by adding a solid "chromatographic" medium (as used in conventional liquid chromatography) such as silica gel or modified silica gel to the sample. However, for conventional high-resolution NMR, this causes excessive line-broadening precluding any diffusion measurement or useful spectral resolution. The use of magic-angle spinning under HR-MAS conditions (FR2847674 and Pages et al. Anal. Chem., 78, 561-566 (2006)) or the use of other techniques like matching the magnetic susceptibility of a solution to the magnetic susceptibility of the silica (WO 2008/050347, Hoffman et al, *J. Magn. Reson* 194, 295-299 (2008)) were suggested for obtaining useful resolved spectra. However, HR-MAS required significant modification to the spectrometer, and also does not guarantee the sample homogeneity necessary when using solid particular matter in the examined sample. Additionally, the rotation causes the diffusion measured to deviate from its non-spinning value.

The conditions required when using susceptibility matching techniques make this method limited in practice. Such conditions include, for example, the use of photosensitive brominated or iodated solvents (due to the high diamagnetic susceptibility of silica gel compared with regular solvents); in addition samples comprising solid silica need instant immediate preparation and constant mixing of said sample prior to the experiment (due to the fact that silica tends to settle or float in solution). In practice, there remains significant broadening of the signals by several Hertz in silica based examples. Additionally, since magnetic susceptibility of a solution is temperature dependent, this ultimately precludes performing DOSY experiments at variable temperatures. All these limitations restrict the range of systems for which silica can be used to separate component mixtures.

There is therefore a need for a liquid medium capable of affording a resolved diffusion ordered spectra of a sample comprising a mixture of compounds that is both stable and less susceptible to magnetic susceptibility effects and limitations.

SUMMARY OF THE INVENTION

In one aspect the invention provides a homogeneous liquid system comprising at least one polar component; at least one non-polar component; and at least one surfactant component; wherein said system is substantially $^1$H-NMR inactive.

The term "homogeneous liquid system" refers to a system which is essentially in a liquid state that is isotropically uniform and has a definite and consistent constitution and physical properties throughout.

When referring to a liquid system of the invention being "substantially $^1$H-NMR inactive" it should be understood to encompass a system which does not afford detectable $^1$H-NMR signals, under $^1$H-NMR spectroscopy measurement (1D-, 2D- or higher dimensional NMR measurement). Systems of the invention which are $^1$H-NMR inactive are substantially devoid of protons in any of said system components. In some embodiments this may be achieved by using a liquid system of the invention, wherein all its components comprise compounds wherein all hydrogen atoms are replaced or substituted by atoms or groups which resonate in a different frequency than the $^1$H nucleus, for example, $^2$H (D), F, Cl, Br, I or any combination thereof.

Such systems of the invention, being substantially $^1$H-NMR inactive may be used for enhancing the diffusion separation of a mixture comprising at least two compounds, and subjecting such a mixture to $^1$H-DOSY spectroscopy. Thus, different compounds in an analyzed mixture, having different diffusion coefficients in a liquid system of the invention, will afford separate $^1$H-DOSY spectra for each compound in said mixture, without interfering (or overlapping) signals from said liquid system.

In another one of its aspects the invention provides a homogeneous liquid system comprising: at least one polar component; at least one non-polar component; and at least one surfactant component; wherein said system is substantially devoid of protons.

When referring to a system being "substantially devoid of protons" it should be understood to encompass a system which its components substantially do not comprise (or are absent of) proton atoms. In some cases this may be achieved by using a liquid system wherein all its components comprise compounds wherein all proton atoms are replaced by different atoms or groups, such as for example, $^2$H (D), F, Cl, Br, I or any combination thereof. In some embodiments such systems may comprise up to 1% proton atoms.

In a further aspect the invention provides a homogeneous liquid system comprising: at least one polar component; at least one non-polar component; and at least one surfactant component; capable of enhancing the diffusion separation of a mixture, said system being substantially devoid of at least one NMR active nucleus present in said mixture.

The term "enhancing the diffusion separation of a mixture", as used herein, should be understood to encompass any enhancement in the differential diffusion of a mixture of at least two compounds in a liquid solvent or a mixture thereof. By enhancing the diffusion separation of a mixture, each compound of said mixture is solvated in a liquid system of the invention to a different extent, depending on differences in diffusion coefficients and/or differences in physical properties (such as for example polarity, solubility, etc.) of said compounds, thereby diffusing differently within said liquid system. In some embodiments said enhancement of diffusion separation of a mixture may be in the range of between about 10 to about 300 as compared with typical NMR solvents. Without being bound by theory, it is expected that different compounds having different diffusion properties in a liquid system of the invention, may exhibit different partitioning between components of the liquid system of the invention thereby also exhibiting enhanced separation in diffusion ordered spectra under suitable conditions.

When referring to a mixture being substantially "devoid of at least one NMR active nucleus present in said mixture" it should be understood to encompass a liquid system of the invention wherein substantially none of its components comprise at least one nucleus which is NMR active, i.e., affords a detectable NMR signal under nuclear magnetic resonance measurements (either in a 1D-, 2D- or higher dimensional NMR measurements), which is present in said mixture capable of being diffusionally separated by said system. Thus, in some embodiments said system components are devoid of at least one NMR active nucleus selected from H, He, C, N, F, Si, P, Fe, Se, Y, Rh, Ag, Cd, Sn, Te, Xe, W, Os, Pt, Hg, Tl and Pb, said nucleus is present in each of said at least two compounds constituting a mixture being diffusionally separated by a system of the invention.

It is noted that nuclei capable of being detected by NMR spectroscopy and are NMR active for their isotopes having a nuclear spin (I) of ?1;2 (which are either naturally abundant or are synthetically enriched). For example the following isotopes of said nuclei are NMR active (i.e. afford a detectable NMR signal): $^{1}H$, $^{3}H$, $^{3}He$, $^{13}C$, $^{19}F$, $^{15}N$, $^{29}Si$, $^{31}P$, $^{57}Fe$, $^{77}Se$, $^{89}Y$, $^{103}Rh$, $^{107}Ag$, $^{109}Ag$, $^{111}Cd$, $^{113}Cd$, $^{117}Sn$, $^{119}Sn$, $^{123}Te$, $^{125}Te$, $^{129}Xe$, $^{183}W$, $^{187}Os$, $^{195}Pt$, $^{199}Hg$, $^{203}Tl$, $^{205}Tl$ and $^{207}Pb$.

Thus, a liquid system of the invention may be used for enhancing the diffusion separation of a mixture comprising at least two compounds each having at least one NMR active nucleus (for example at least one of H, He, C, N, F, Si, P, Fe, Se, Y, Rh, Ag, Cd, Sn, Te, Xe, W, Os, Pt, Hg, Tl and Pb), which is substantially absent from components of said liquid system, and subjecting such a mixture to either $^{1}H$, $^{3}H$, $^{3}He$, $^{13}C$, $^{19}F$, $^{15}N$, $^{29}Si$, $^{31}P$, $^{57}Fe$, $^{77}Se$, $^{89}Y$, $^{103}Rh$, $^{107}Ag$, $^{109}Ag$, $^{111}Cd$, $^{113}Cd$, $^{117}Sn$, $^{119}Sn$, $^{123}Te$, $^{125}Te$, $^{129}Xe$, $^{183}W$, $^{187}Os$, $^{195}Pt$, $^{199}Hg$, $^{203}Tl$, $^{205}Tl$, or $^{207}Pb$-DOSY spectroscopy. Thus, different compounds in an analyzed mixture, having different diffusion coefficients in a liquid system of the invention, will afford separate $^{1}H$, $^{3}H$, $^{3}He$, $^{13}C$, $^{19}F$, $^{15}N$, $^{29}Si$, $^{31}P$, $^{57}Fe$, $^{77}Se$, $^{89}Y$, $^{103}Rh$, $^{107}Ag$, $^{109}Ag$, $^{111}Cd$, $^{113}Cd$, $^{117}Sn$, $^{119}Sn$, $^{123}Te$, $^{125}Te$, $^{129}Xe$, $^{183}W$, $^{187}Os$, $^{195}Pt$, $^{199}Hg$, $^{203}Tl$, $^{205}Tl$ or $^{207}Pb$ spectra for each compound in said mixture, without interfering signals from liquid system of the invention.

When referring to a "polar component" of a liquid system of the invention, it should be understood to encompass any polar solvent having a dipole moment substantially above zero. In some embodiments, said at least one polar component comprises at least one solvent selected from water, straight, branched, saturated, unsaturated or aromatic $C_1$-$C_{20}$ alcohol (including a polyol) or any combinations thereof, said at least one solvent being substantially fully deuterated, perhalogenated or any combination thereof.

In some other embodiments, said polar component may be selected from the following non-limiting list: $D_2O$, isopropanol-$d_8$, methanol-$d_4$, ethanol-$d_6$, 2,2,2-trifluoroethanol-$d_3$, tertbutanol-$d_{10}$ ethylene glycol-$d_6$, propylene glycol-$d_8$ and glycerol-$d_8$ or any combination thereof.

When referring to a "non-polar" component of a liquid system of the invention it should be understood to encompass any solvent substantially devoid of dipole moment, being substantially immisible in said at least one polar component.

In some embodiments said at least one non-polar component comprises at least one hydrocarbon being substantially fully deuterated, perhalogenated or any combination thereof selected from straight, branched, cyclic or polycyclic alkane, alkene or alkyne, $C_3$-$C_{120}$ aromatic ring system or any combination thereof.

Non-limiting examples of the non-polar component include: chloroform, methylene chloride, hexane, triglycerides, diglycerides, fat, oil, long chain saturated or unsaturated fatty acids (such as for example hexadecanoic acid), limonene, silicone oil, fluorocarbons, freons, CFC's, etc. being either fully deuterated, perhalogenated or any combination thereof.

In some embodiments, a non-polar component of a liquid system of the invention may be selected from the following non-limiting list: 1-bromoperfluoroheptane, 1-bromoperfluorooctane, perfluorohexane, perfluoroheptane, perfluorooctane, perfluorocyclohexane, other halogenated derivatives or any combination thereof.

The term "surfactant" as used herein is meant to encompass an amphiphilic substance which is capable of lowering the surface tension of a liquid and/or the interfacial tension between two or more immisible liquids and/or gases.

In some embodiments said at least one surfactant component comprises at least one compound selected from anionic, cationic, zwitterionic (amphoteric), non-ionic, surfactant being substantially fully deuterated, perhalogenated or any combination thereof.

A surfactant employed by a system of the present invention is either substantially fully deuterated and/or perhalogenated surfactant, of the following non limiting list: perfluorooctanoate (PFOA or PFO), perfluorooctanesulfonate (PFOS), sodium dodecyl sulfate (SDS), ammonium lauryl sulfate, and other alkyl sulfate salts, sodium laureth sulfate, sodium lauryl ether sulfate (SLES), alkyl benzene sulfonate, soaps, or fatty acid salts, cetyl trimethylammoniun bromide (CTAB), hexadecyl trimethyl ammonium bromide, and other alkyltrimethylammonium salts, cetylpyridinium chloride (CPC), polyethoxylated tallow amine (POEA), benzalkonium chloride (BAC), benzethonium chloride (BZT), dodecyl betaine, cocamidopropyl betaine, coco ampho glycinate, alkyl poly(ethylene oxide), alkylphenol poly(ethylene oxide), copolymers of poly(ethylene oxide) and polypropylene oxide) (poloxamers or poloxamines), alkyl polyglucosides (such as for example octyl glucoside, decyl maltoside), nonylphenol ethoxylates, fatty alcohols (such as for example cetyl alcohol, oleyl alcohol), cocamide MEA, cocamide DEA, polysorbates (Tween 20, Tween 80, dodecyl dimethylamine oxide) or any combination thereof.

In some embodiments, an surfactant component of a liquid system of the invention is a substantially fully deuterated, perhalogenated or any combination thereof anionic surfactant selected from the following non-limiting list including: sulfate ($-OSO_3$), sulfonate ($-SO_2O^-$), carboxylate ($-CO_2O^-$), phosphate ($-OPO_3^-$), phosphonate ($-PO_3^-$) derivative of a straight, branched, saturated, unsaturated or aromatic $C_1$-$C_{120}$ carboxylic acid and $C_1$-$C_{120}$ betaine.

In other embodiments a surfactant component of the invention may be selected from the following non-limiting list: perfluorohexanoate, perfluoroheptanoate, perfluorooctanoate, perfluorononoate, perfluorodecanoate, perfluoroundecanoate, perfluorododecanoate, perfluorotridecanoate, perfluorotetradecanoate, perfluoropentadecanoate, perfluorohexadecanoate, their chloro and other halo derivatives, unsaturated, aromatics, branched, cyclic and polycyclic derivatives thereof and any combination thereof.

The above noted anionic derivatives may include as counter ion any positively charged ion selected from but not limited to lithium, sodium, potassium, rubidium, cesium, magnesium, calcium, strontium and barium. The invention further includes as an surfactant component the free fully deuterated or perhalogenated acid of the above mentioned salts.

When referring to a component being "substantially fully deuterated, perhalogenated or any combination thereof" it should be understood to encompass a component of a liquid system of the invention for which substantially all hydrogen atoms are replaced with an atom selected from deuterium, fluorine, chlorine, bromine, iodine or any combination thereof. In some embodiments such a system may comprise up to 1% proton atoms.

In one embodiment, said polar component comprises $D_2O$ and at least one fully deuterated alcohol. In another embodiment said non-polar component comprises at least one perhalogenated hydrocarbon (oil). In a further embodiment said surfactant component comprises at least one perfluorinated surfactant.

In another embodiment, a liquid system of the invention is an emulsion, a micro-emulsion, mini-emulsion, nano-emulsion, a double emulsion, liposomal system, lyotropic liquid crystals, organogels or any combination thereof or any other type of micro- or nanostructured liquid.

The emulsions may include but not be limited to the forms O/W, W/O, W/O/W, O/W/O, $W/O_1/O_2$, $W/O_2/O_1$, $O_1/W/O_2$, $O_1/O_2/W$, $O_2/O_1/W$, $O_2/W/O_1$ and combinations of these forms with bicontinuous phases. The term "micro-emulsion" refers to thermodynamically stable self-assembled micro or nano-droplets or other structures of immiscible oil and water or water-like liquid dispersions in the presence of surfactants.

The invention further provides a liquid system of the invention, for use in enhancing the diffusion separation of a mixture.

In a further aspect the invention provides a liquid system of the invention for use in generating a diffusion ordered spectrum of a sample comprising at least two compounds.

In some embodiments, said spectrum is selected from a $^1H$, $^3H$, $^3He$, $^{13}C$, $^{19}F$, $^{15}N$, $^{29}Si$, $^{31}P$, $^{57}Fe$, $^{77}Se$, $^{89}Y$, $^{103}Rh$, $^{107}Ag$, $^{109}Ag$, $^{111}Cd$, $^{113}Cd$, $^{117}Sn$, $^{119}Sn$, $^{123}Te$, $^{125}Te$, $^{129}Xe$, $^{183}W$, $^{187}Os$, $^{195}Pt$, $^{199}Hg$, $^{203}Tl$, $^{205}Tl$, $^{207}Pb$-diffusion ordered spectra of said sample. In other embodiments said spectrum is a $^1H$ diffusion ordered spectrum of said sample. In yet further embodiments, said spectrum is a $^{19}F$ diffusion ordered spectrum of said sample. In other embodiments said spectrum is a $^{31}P$ diffusion ordered spectrum of said sample.

In another one of its aspects the invention provides a method of enhancing the diffusion separation of a mixture comprising: (a) providing a liquid system of the invention; and (b) mixing said system with said mixture.

In a further aspect, the invention provides a method of generating a diffusion ordered spectrum of a mixture comprising at least two compounds, said method comprising: (a) providing a liquid system of the invention; (b) combining said system with said mixture; (c) subjecting combination to diffusion ordered spectroscopy; (d) obtaining a diffusion ordered spectrum of said mixture; (e) processing the spectrum to yield separate spectra of each compound of said mixture.

In another one of its aspects the invention provides a method of minimizing the peak width in a liquid state diffusion ordered spectrum of a mixture comprising at least two compounds, said method comprising: (a) providing a liquid system of the invention; (b) combining said system with said mixture; (c) subjecting combination to diffusion ordered spectroscopy; (d) obtaining a diffusion ordered spectrum of said mixture; (e) processing said spectrum to yield separate spectra of each compound of said mixture.

In one embodiment a method of the invention further comprises the step of selecting a liquid system, being substantially devoid of at least one NMR active nucleus present in said mixture. In another embodiment said NMR active nucleus is selected from H, He, C, N, F, Si, P, Fe, Se, Y, Rh, Ag, Cd, Sn, Te, Xe, W, Os, Pt, Hg, Tl and Pb.

Any of the above noted methods of the invention may be carried out at a series of different temperatures of a sample mixed with a liquid system of the invention, and/or with the addition of changing at least one physical attribute of a system of the invention (for example the concentration and/or pressure). One, non-limiting, example would be to use an emulsion that changes from O/W to W/O (or vice versa) upon temperature change which may afford a change in relative diffusion rates between different compounds in solution.

In one embodiment said diffusion ordered spectroscopy is selected from a group consisting of DOSY, DDCOSY, $T_1$-$T_2$ correlation spectroscopy, RDCOSY, DEXSY, INEPT-DOSY, DEPT-DOSY, MQF-DOSY, COSY-DOSY, TOCSY-DOSY, HMQC-DOSY, CIDNP-DOSY and DNP-DOSY.

Where the diffusion ordered spectroscopy measurements, in accordance with method of the invention, are of nucleus other than $^1H$, than a mixture being diffusionally separated by a liquid system of the invention may comprise at least one of $^3H$, He, C, N, F, Si, P, Fe, Se, Y, Rh, Ag, Cd, Sn, Te, Xe, W, Os, Pt, Hg, Tl and Pb or another NMR active nucleus. Said nucleus should be substantially absent from a liquid system used by said methods of the invention.

The term "diffusion ordered spectroscopy (DOSY)" as used herein denotes a spectrum achieved by any single or multidimensional combination of relaxation and/or diffusion ordered spectroscopy including but not limited to DDCOSY (Callaghan et al. *J Chem. Phys.* 120:4032-4038 (2004) and Qiao *Biophys. J* 89:2899-2905 (2005)), $T_1$-$T_2$ correlation (Song et al. *J Magn. Reson.* 154:261-268 (2002)), RDCOSY and DEXSY (Qiao et al. *J Chem. Phys.* 122:214912 (2005)). In all the above mentioned spectroscopic methods the chemical shift may be plotted against relaxation time, be it transverse ($T_2$), longitudinal ($T_1$), rotational ($T_{1\rho}$), Zeeman ($T_{1Z}$) or quadrupolar ($T_{1Q}$) relaxation. Additionally, the diffusion or relaxation or a combination thereof or exchange or combination ordered spectroscopy technique may include in a non-limiting manner spin-echo, stimulated echo, symmetric or asymmetric bipolar stimulated echo, symmetric or asymmetric bipolar LED, convection compensated and all variants of relaxation experiments.

The diffusion ordered spectroscopic techniques suitable for the invention may also include any combinations of DOSY and relaxation experiments and their variants of DOSY and IDOSY with other NMR pulse sequences including but not limited to 2DJ-IDOSY (Nilsson M L et al. *Anal. Chem.* 76:5418-5422 (2004)), DOSY-COSY, DOSY-TOCSY (Jerschow A et al. *J. Magn. Reson. A,* 123:222-225 (1996)), DOSY-NOESY (Gozansky E K et al. *J Maga. Reson. B* 111:94-96 (1996)), DOSY-ROESY, DOSY-HMQC (Barjat H et al. *J Maga. Reson.*, 131:131-138 (1998)), DOSY-HSQC (Buevich A V et al. *J Am. Chem. Soc.*, 124:7156-7162 (2002)), DOSY-HMBC, DQ-DOSY (Birlirakis Net al. *J. Am. Chem. Soc.* 118:13083-13084 (1996)), DEPT-DOSY, INEPT-DOSY (Wu D et al. *J. Magn. Reson. A* 123:215-218 (1996)), CIDNP-DOSY. DNP-DOSY (Odintsov, et al. *J. Maga. Res.*, 135, 435-443 (1998)), and higher dimensional combinations thereof.

The term "diffusion ordered spectrum peak" relates to a chemical shift signal measured in ppm, which is detected for a compound in a mixture, by any diffusion ordered spectrum indicated above.

The width of the peak or signal is measured in Hz. Without the use of a liquid system of the invention the peak width of compounds in a mixture, may be between 100 to 2000 Hz. This value range is considered to be broad thereby not permitting accurate differentiation of the components of the sample. Upon using a liquid system of the invention in accordance with a method of the invention, the peak width may be minimized or narrowed by at least 100 to 1000 times compared to a suspension system comprising silica particulate, corresponding to peak width not greater than 0.3 Hz broader than conventional solution spectroscopy.

In another one of its aspects the invention provides a kit comprising at least one container comprising at least one polar component; at least one non-polar component and at least one surfactant component; wherein said components are substantially $^1$H-NMR inactive; and optionally instructions and means for their use in carrying out a liquid state diffusion ordered spectroscopy.

In one embodiment of said kit, at least one container comprising components of liquid system of the invention may be an NMR tube (possibly dispensable), which may be sealed. In some other embodiments, said means comprised in said kit include for example: an NMR tube, a spatula for adding the solid sample and a pipette or syringe for transferring the liquid, a container with a built in transfer mechanism for placing into an NMR tube.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

The present invention provides a method for analyzing mixtures of compounds by 2D-NMR spectroscopy. The method separates the compounds spectroscopically using differences in their diffusion characteristics in a liquid system of the invention.

A liquid system of the invention is capable of increasing the separation in the diffusion dimension using a stable, completely liquid system while maintaining full resolution typical of a regular high-resolution NMR experiment, without resorting to solid-state techniques.

Without being bound by theory it should be mentioned that the use of a liquid system of the invention for differential dissolution of a mixture comprising at least two compounds having different dissolution properties, and subjecting such a mixture to diffusion ordered spectroscopy has several advantages over the use of a suspension comprising solid particles such as silica, such as for example: easier control of droplet size in an emulsion formulation (as opposed to particle size in a suspension), the magnetic susceptibility of emulsion droplets in a system of the invention is closer to the magnetic susceptibility of typical solvents, therefore no predetermination of components of the system to be defined prior to the execution of a diffusion ordered experiment of a sample is needed. The line-width of a signal in a DOSY spectrum of a sample comprising a mixture is much less dependent on the magnetic susceptibility difference between the phases (as compared to suspensions comprising silica particles). Variable temperature experiments can be carried out for a single sample and additionally, liquid systems of the invention are stable.

In a preliminary $^{19}$F self-diffusion measurements, a mixture of four compounds having different polar properties was used:
a non-polar perflourohexane ($C_6F_{14}$),
a polar sparingly soluble in water 2,4-dinitrofluorobenzene ($C_6H_3FN_2O_4$),
an amphiphilic fluorosurfactant (FSN) and
highly polar and water soluble fluoride.
This mixture was tested with a liquid system comprising:
one phase (oily) comprising Tween 60:(R)-limonine:ethanol (14:3:3) and
a second phase (aqueous) comprising water:propylene glycol (1:1)
(WO20051206 and Kogan et al. *J. Disp. Sci. Tech.*, 28, 1008-1019 (2007)).

Figure 1:
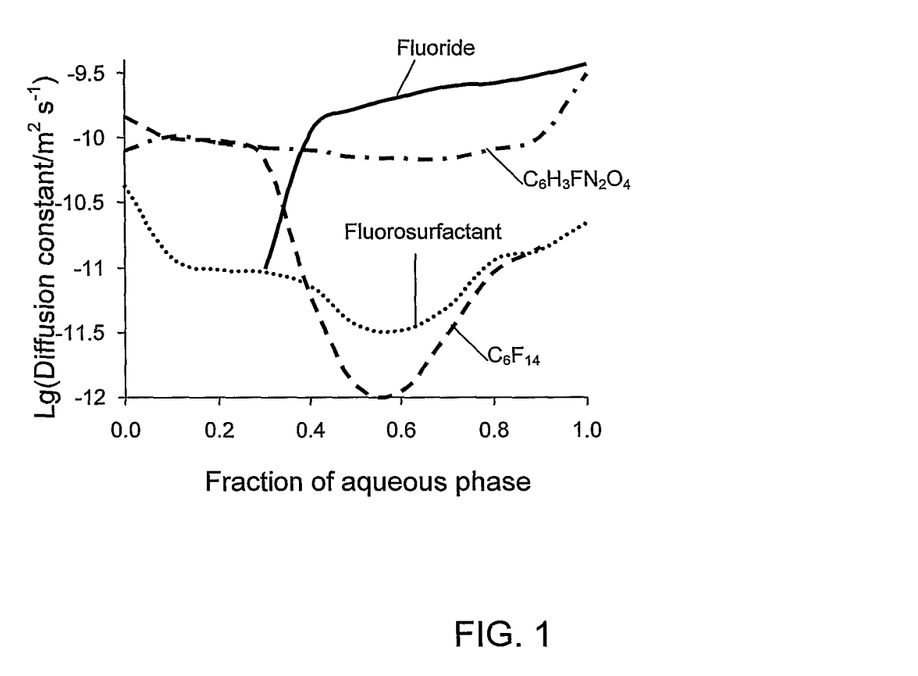
FIG. 1 shows the diffusion behavior of a mixture comprising perflourohexane ($C_6F_{14}$) and 2,4-dinitrofluorobenzene ($C_6H_3FN_2O_4$) a fluorosurfactant (FSN) and fluoride along the dilution line of a microemulsion comprising Tween60:R-limonine:ethanol (14:3:3) and the aqueous phase was water:propylene glycol (1:1).

$^{19}$F self-diffusion measurements (FIG. 1) were made along the dilution line. For aqueous phase fractions less than 0.35, the phase is W/O (water in oil); up to 0.8 it is bicontinuous and above that it is O/W (oil in water). FIG. 1 shows that the four compounds have different behaviors along the dilution line.

The amphiphilic flourosurfactant is located persistently at the interface between the oily and aqueous phases. In the pure oily and pure aqueous phases at the ends of the dilution line, the fluorosurfactant forms its own micelles. As a result its diffusion is persistently slow but more so in the bicontinuous phase between 35 and 80% water. The 2,4-dinitrofluorobenzene diffuses rapidly in the W/O region, less so in the O/W region and slowest in the bicontinuous region. This indicates that it is preferentially located in the oily phase or at the interface of the oily droplets. The fluoride diffuses rapidly except in the W/O region indicating that, as expected, it prefers to reside in the aqueous phase. The perflourohexane consistently diffuses rapidly indicating that it has no preference to oil or water and that it interacts only weakly with the solvent.

This preliminary example shows that each type (W/O, bicontinuous and O/W) of a microemulsion can be used to separate different molecules based on their different physical properties (such as for example their different polarities).

Another exemplary liquid system of the invention is a microemulsion comprising isopropanol, water, perfluorododecanoic acid (and its lithium and sodium salts) and 1-bromoperfluoroheptane.

Figure 2:
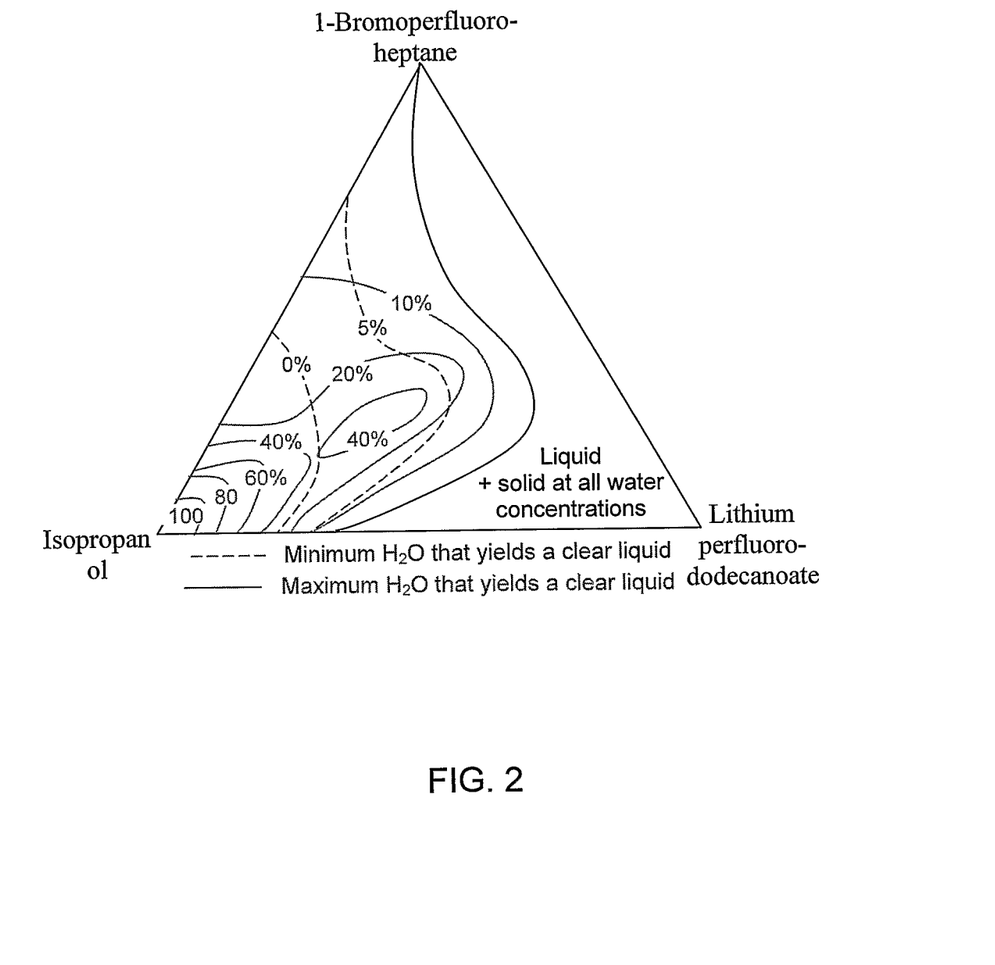
FIG. 2 shows a phase diagram for a liquid system comprising isopropanol, water, lithium perfluorododecanoate and 1-bromoperfluoroheptane.
Figure 3:
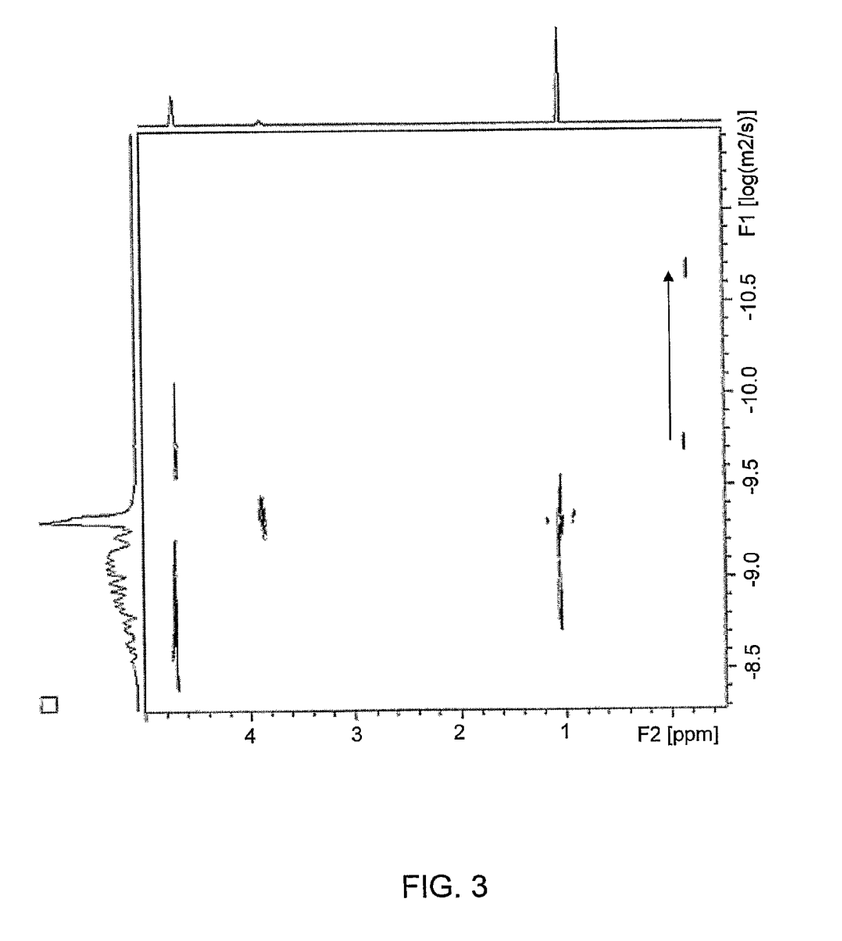
FIG. 3 shows an $^1$H-DOSY spectrum of hexmethyl disiloxane and DSS using a microemulsion consisting of water (63% w/w), isopropanol (25%), sodium perfluorododecanoate (8%) and 1-bromoperfluoroheptane (4%). Arrow pointing to separation between signals of hexamethyl disiloxane and DSS due to the use of defined microemulsion.

FIG. 2 shows a phase diagram for a mixture of isopropanol, water, lithium perfluorododecanoate and 1-bromoperfluoroheptane. The suitability of these microemulsions for diffusion ordered NMR spectroscopy was tested with a sample mixture comprising hexamethyl disiloxane (non-polar compound) and DSS (trimethylpentane sulfonic acid sodium salt) (polar compound). FIG. 3 shows the separation of hexamethyl disiloxane and DSS in a DOSY spectrum, using a microemulsion consisting of water (63% w/w), isopropanol (25%), sodium perfluorododecanoate (8%) and 1-bromoperfluoroheptane (4%).

Figure 4:
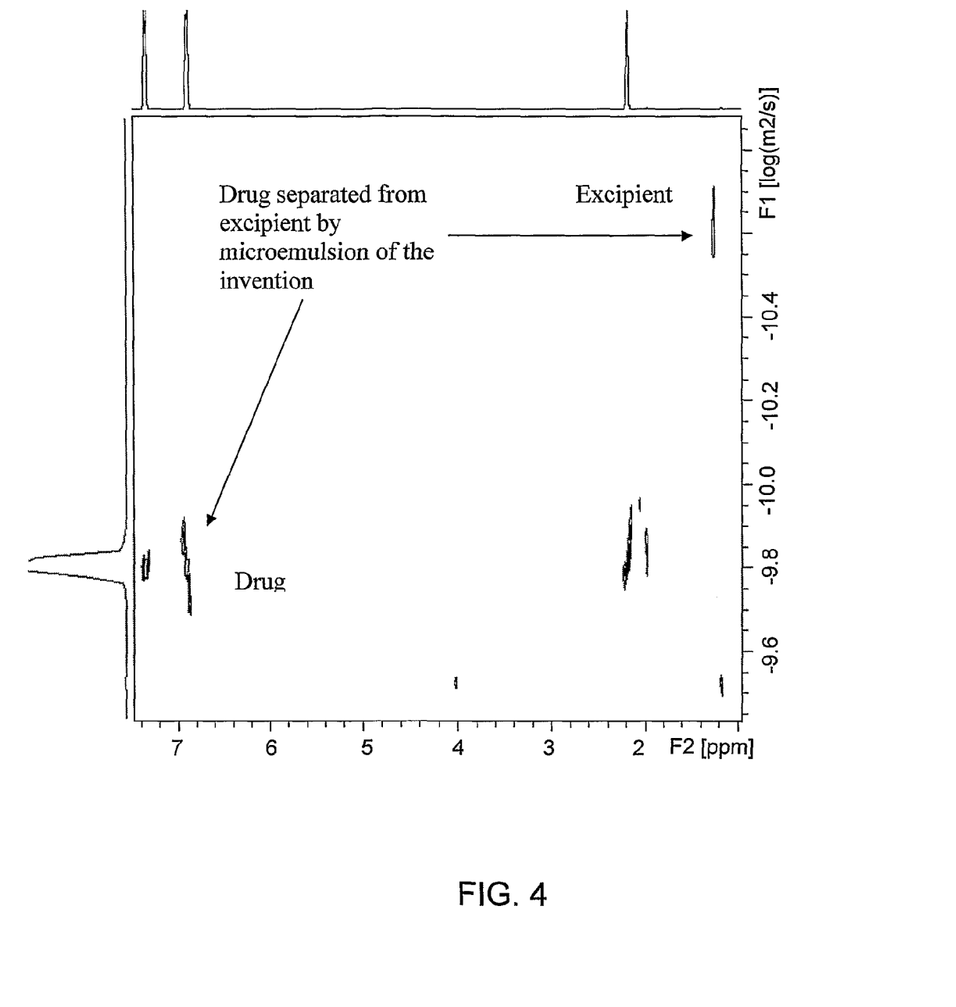
FIG. 4 shows an $^1$H-DOSY spectrum of a paracetamol tablet (including its excipients) dissolved in a liquid system comprising $D_2O$ (53% w/w), isopropanol-$d_8$ (25%), lithium perfluorododecanoate (15%) and 1-bromoperfluoroheptane (7%).

FIG. 4 shows the DOSY separation of a fully deprotonated liquid system comprising $D_2O$ (53% w/w), isopropanol-$d_8$ (25%), lithium perfluorododecanoate (15%) and 1-bromoperfluoroheptane (7%) was tested by dissolving a paracetamol tablet. The spectrum in FIG. 4 shows the NMR signal of the drug molecule clearly separated from the signals of its magnesium stearate excipient (binder).

Figure 5:
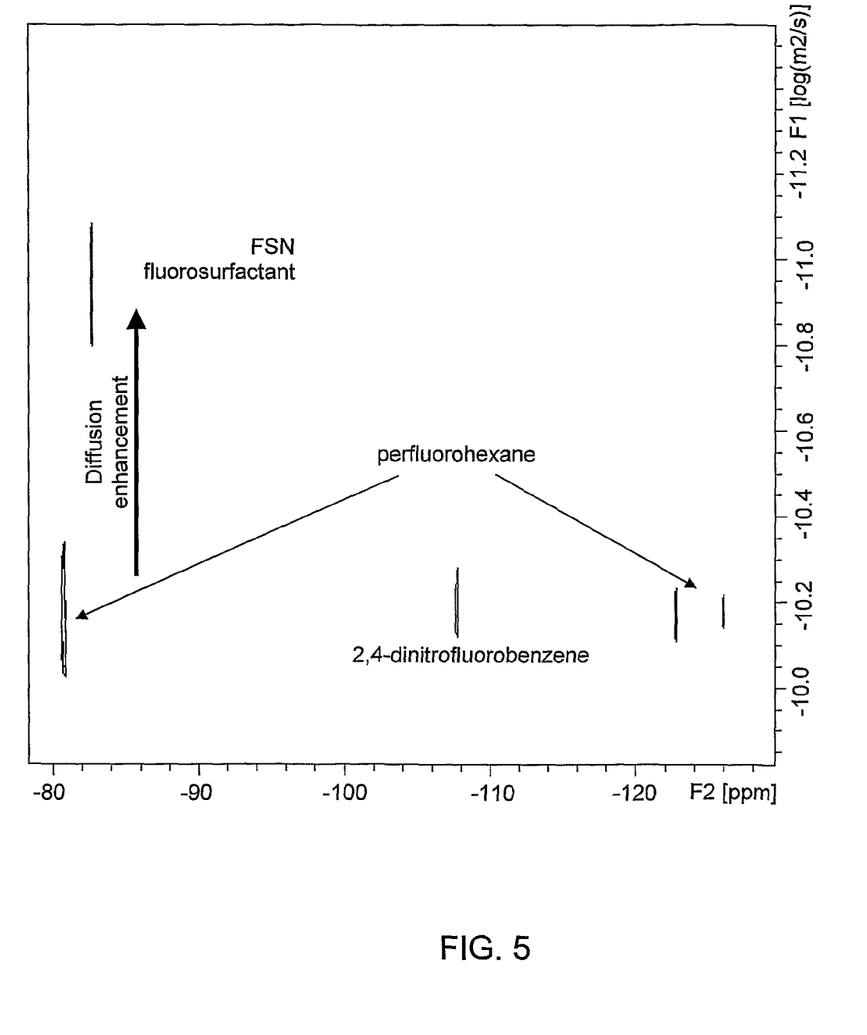
FIG. 5 shows the $^{19}$F-DOSY of a mixture comprising FSN fluorosurfactant, perfluorohexane and 2,4-dinitrofluorobenzene in a liquid system being a O/W/O double emulsion, comprising an 1:1 canola oil: water phase (pH=7 $KH_2PO_4$, buffer (20%)) in an intermediate phase of 6% solution of whey protein isolate in water. This emulsion comprises 20% of the outer oily phase that comprises 1.25% sodium caseanate and 5% polyglycerine polyricinoleate in canola oil.

A similar strong effect has also been observed (FIG. 5) for FSN fluorosurfactant in an O/W/O double emulsion comprising an internal oily phase of 1:1 canola oil: water with pH7 $KH_2PO_4$ buffer (20%) in an intermediate aqueous phase of 6% solution of whey protein isolate in water. This emulsion comprises 20% of the outer oily phase that comprises 1.25% sodium caseanate and 5% polyglycerine polyricinoleate in canola oil.

The invention claimed is:

1. A homogeneous liquid system, comprising:
   at least one polar component;
   at least one non-polar component; and
   at least one surfactant component;
   wherein said system has at least one of the following characteristics:
   the system is substantially $^1$H-NMR inactive;
   the system is substantially devoid of protons; and
   the system is capable of enhancing the diffusion separation of a mixture, the system being substantially devoid of at least one NMR active nucleus present in the mixture.

2. The liquid system according to claim 1, wherein the at least one NMR active nucleus is selected from the group consisting of H, He, C, N, F, Si, P, Fe, Se, Y, Rh, Ag, Cd, Sn, Te, Xe, W, Os, Pt, Hg, Tl and Pb.

3. The liquid system according to claim 1, wherein the at least one polar component comprises at least one solvent selected from the group consisting of water; a straight, branched, saturated, unsaturated or aromatic $C_1$-$C_{20}$ alcohol; and any combinations thereof, the at least one solvent being substantially fully deuterated, perhalogenated or any combination thereof.

4. The liquid system according to claim 1, wherein the at least one polar component is selected from the group consisting of $D_2O$, isopropanol-$d_8$, methanol-$d_4$, ethanol-$d_6$, 2,2,2-trifluoroethanol-$d_3$, tertbutanol-$d_{10}$ ethylene glycol-$d_6$, propylene glycol-$d_8$, glycerol-$d_8$, and any combination thereof.

5. The liquid system according to claim 1, wherein the at least one non-polar component comprises at least one hydrocarbon being substantially fully deuterated, perhalogenated, or any combination thereof selected from the group consisting of straight, branched, cyclic or polycyclic $C_1$-$C_{120}$ alkane, alkene or alkyne; a $C_3$-$C_{120}$ aromatic ring system, and any combination thereof.

6. The liquid system according to claim 1, wherein the at least one non-polar component is selected from the group consisting of 1-bromoperfluoroheptane, 1-bromoperfluorooctane, perfluorohexane, perfluoroheptane, perfluorooctane, perfluorocyclohexane, and any combination thereof.

7. The liquid system according to claim 1, wherein the at least one surfactant component comprises at least one compound selected from the group consisting of an anionic, a cationic, a zwitterionic, and a non-ionic, surfactant being substantially fully deuterated, perhalogenated, or any combination thereof.

8. The liquid system according to claim 1, wherein the at least one surfactant component is selected from the group consisting of perfluorohexanoate, perfluoroheptanoate, perfluorooctanoate, perfluorononoate, perfluorodecanoate, perfluoroundecanoate, perfluorododecanoate, perfluorotridecanoate, perfluorotetradecanoate, perfluoropentadecanoate, perfluorohexadecanoate, and any combination thereof.

9. The liquid system according to claim 1, being an emulsion, a microemulsion, a double emulsion, or any combination thereof, or any other type of micro- or nanostructured liquid.

10. The liquid system according to claim 1, wherein the at least one polar component comprises $D_2O$ and at least one fully deuterated alcohol.

11. The liquid system according to claim 1, wherein the at least one non-polar component comprises at least perhalogenated hydrocarbon.

12. The liquid system according to claim 1, wherein the at least one surfactant component comprises at least one perfluorinated or haloperfluorinated surfactant.

13. A method of enhancing the diffusion separation of a mixture of at least two compounds, the method comprising: (a) providing a liquid system according to claim 1; and (b) mixing the system with the mixture of at least two compounds.

14. A method for at least one of:
   generating a diffusion ordered spectrum of a mixture comprising at least two compounds, and
   minimizing the peak width in a liquid state diffusion ordered spectrum of a mixture comprising at least two compounds;
   the method comprising: (a) providing a liquid system according to claim 1; (b) combining the system with the mixture of two compounds to form a combination; (c) subjecting the combination to diffusion ordered spectroscopy; (d) obtaining a diffusion ordered spectrum of the mixture; (e) processing the spectrum to yield separate spectra of each compound of the mixture.

15. The method according to claim 14, further comprising the step of selecting a liquid system, being substantially devoid of at least one NMR active nucleus present in the mixture.

16. The method according to claim 14, further comprising the step of selecting a liquid system, being substantially devoid of at least one NMR active nucleus selected from the group consisting of H, He, C, N, F, Si, P, Fe, Se, Y, Rh, Ag, Cd, Sn, Te, Xe, W, Os, Pt, Hg, Tl, and Pb.

17. The method according to claim 14, wherein the diffusion ordered spectrum is at least one member selected from the group consisting of $^{1}$H, $^{3}$H, $^{3}$He, $^{13}$C, $^{19}$F, $^{15}$N, $^{29}$Si, $^{31}$P, $^{57}$Fe, $^{77}$Se, $^{89}$Y, $^{103}$Rh, $^{107}$Ag, $^{109}$Ag, $^{111}$Cd, $^{113}$Cd, $^{117}$Sn, $^{119}$Sn, $^{123}$Te, $^{125}$Te, $^{129}$Xe, $^{183}$W, $^{187}$Os, $^{195}$Pt, $^{199}$Hg, $^{203}$Tl, $^{205}$Tl, and $^{207}$Pb-diffusion ordered spectrum of the mixture.

18. The method according to claim 14, wherein the diffusion ordered spectrum is obtained via NMR spectroscopy selected from the group consisting of DOSY, DDCOSY, $T_1$-$T_2$ correlation spectroscopy, RDCOSY, DEXSY, INEPT-DOSY, DEPT-DOSY, MQF-DOSY, COSY-DOSY, TOCSY-DOSY, HMQC-DOSY, CIDNP-DOSY, and DNP-DOSY.

19. A kit comprising at least one container comprising a liquid system according to claim 1; and optionally instructions and means for their use in carrying out a liquid state diffusion ordered spectroscopy.

\* \* \* \* \*